United States Patent
Ikegami et al.

(10) Patent No.: US 7,361,679 B2
(45) Date of Patent: Apr. 22, 2008

(54) 2-PHENYL-3-HETEROARYLPROPIONIC ACID DERIVATIVE OR SALT THEREOF AND MEDICINE CONTAINING THE SAME

(75) Inventors: Satoru Ikegami, Kyoto (JP); Yoichiro Hoshina, Kyoto (JP)

(73) Assignee: Kaken Pharmaceutical Co., Ltd. (JP)

( * ) Notice: Subject to any disclaimer, the term of this patent is extended or adjusted under 35 U.S.C. 154(b) by 248 days.

(21) Appl. No.: 10/489,114

(22) PCT Filed: Sep. 3, 2002

(86) PCT No.: PCT/JP02/08921

§ 371 (c)(1),
(2), (4) Date: Jul. 27, 2004

(87) PCT Pub. No.: WO03/024933

PCT Pub. Date: Mar. 27, 2003

(65) Prior Publication Data

US 2004/0259908 A1  Dec. 23, 2004

(30) Foreign Application Priority Data

Sep. 12, 2001 (JP) .............................. 2001-276371

(51) Int. Cl.
  *A61K 31/415* (2006.01)
  *A61K 31/34* (2006.01)
  *C07D 307/02* (2006.01)
  *C07D 231/10* (2006.01)

(52) U.S. Cl. ...................... 514/406; 514/461; 549/501; 548/377.1

(58) Field of Classification Search ................ 514/461, 514/406; 549/501; 548/377.1
See application file for complete search history.

(56) References Cited

FOREIGN PATENT DOCUMENTS

| EP | 0293220 B1 | * | 5/1988 |
| EP | 293220 | | 11/1988 |
| GB | 1097596 | | 1/1968 |
| WO | WO 98/08840 | | 3/1998 |
| WO | WO 99/06433 | | 2/1999 |
| WO | WO 99/62901 | | 12/1999 |
| WO | WO 99/64390 | | 12/1999 |

OTHER PUBLICATIONS

Hcaplus 78:58183.*
Durant et. al., "Nonsteroidal Antiinflammatory Agents. Some Arylacetic Acids", Journal of Medicinal Chemistry (1965), 8(5), 598-603.*
Hcaplus 143:95268.*
Lobb et. al., "Small molecule antagonists of alpha 4 integrins: novel drugs for asthma", Expert Opinion on Investigational Drugs (1999) 8(7):935-945.*

* cited by examiner

Primary Examiner—Janet L. Andres
Assistant Examiner—Binta Robinson
(74) Attorney, Agent, or Firm—Nixon Peabody LLP

(57) ABSTRACT

The present invention relates to a 2-phenyl-3-heteroarylpropionic acid derivative or a salt thereof, and also relates to a pharmaceutical agent and a VLA-4 and/or LPAM-1 antagonist each of which contains the same as an active ingredient.

3 Claims, No Drawings

2-PHENYL-3-HETEROARYLPROPIONIC ACID DERIVATIVE OR SALT THEREOF AND MEDICINE CONTAINING THE SAME

CROSS-REFERENCE TO RELATED APPLICATIONS

This application is a 371 National Phase Entry Application of co-pending International Application PCT/JP02/08921, filed 3 Sep. 2002, which designated the U.S. and which claims the benefit under 35 U.S.C. § 119 of Japanese Patent Application No. 2001-276371, filed 12 Sep. 2001.

TECHNICAL FIELD

The present invention relates to a novel 2-phenyl-3-heteroarylpropionic acid derivative or a salt thereof and a pharmaceutical agent containing the same as an active ingredient and a cell adhesion inhibitor.

TECHNICAL BACKGROUND

An adhesion phenomenon is essential to a complicated life phenomenon resulted from intercellular interaction such as activation, migration, proliferation, differentiation, etc., of cells. And, cell adhesion molecules classified as integrin, immunoglobulin, selectin, cadherin, etc., are involved in the above cell-cell or cell-extracellular matrix interactions. The integrin family has an αβ-heterodimer structure and 16 different integrin α chains and 8 different integrin β chains have been identified. Integrin VLA-4 (α4β1) as one of them expresses within lymphocyte, eosinophils, basophils and monocyte, and VCAM-1 and fibronectin are ligands thereof. That is, VLA-4 plays an important role in cell-cell interactions and cell-extracellular matrix interactions mediated by VCAM-1 and fibronectin. Further, integrin LPAM-1 (α4β7) expresses within lymphocyte, eosinophils, basophils and monocyte, and VCAM-1, fibronectin and MadCAM-1 are ligands thereof. Meanwhile, for leucocytes' functioning in the inflammatory tissue, leucocytes circulating with blood are required to pass through the vascular endothelial cells and infiltrate the inflammatory site. Binding of either VLA-4 or LPAM-1 with either VCAM-1 or MadCAM-1 is one of the most important mechanisms that produce an intense adhesion between leukocytes and vascular endothelial cells. Inflammatory cells such as T lymphocyte, B lymphocyte, monocyte and eosinophils express VLA-4 and LPAM-1, and VLA-4 and LPAM-1 strongly take part in the infiltration of these cells to an inflammatory lesion. The adhesion molecules play an essential role in the activation of cells through cell-cell interactions, and it has been made clear that the VLA-4/VCAM-1 mechanism activates eosinophils to cause degranulation, and that a signal through VLA-4 takes part in the activation of antigen-specific proliferation of lymphocytes as well.

For elucidating the roles of VLA-4 and LPAM-1 in an inflammation, several studies have been made to inhibit this intermolecular binding using monoclonal antibody. For example, an anti-α4 monoclonal antibody inhibits the adhesion of VLA-4 expressing Ramos cells onto human umbilical venous endothelial cells (HUVEC) or VCAM-1-gene-transferred COS cells. The antibody has shown therapeutic and/or prophylactic effects in several animal models. For example, significant effects have been demonstrated on a rat adjuvant induced arthritis model (Barbadillo et al., Arthritis Rheumatol., 1993, 36, 95), and contact hypersensitivity and delayed-type hypersensitivity model (Ferguson and Kupper, J. Immunol., 1993, 150, 1172; Chisholm et al., Eur. J. Immunol., 1993, 23, 682). Further, the action of the antibody has been evaluated on experimental autoimmune encephalomyelitis (Yednock, Nature, 1992, 356, 63), asthma model (Abraham et al., J. Clin. Invest., 1993, 93, 776) and inflammatory bowel disease (IBD) model (Podolsky et al., J. Clin. Invest., 1993, 92, 372). Further, it has been shown that the cell adhesion with VLA-4 plays some roles in rheumatoid arthritis, nephritis, diabetes, systemic lupus erythematosus, delayed-type allergy, multiple sclerosis, arteriosclerosis, organ transparent and various malignant tumors.

Therefore, blocking of VLA-4 (α4β1) and/or LPAM-1 (α4β7) integrins with an appropriate antagonist is effective for the therapeutical treatment of the above various diseases including inflammation diseases.

Several low-molecular-weight compounds have been already proposed as VLA-4 and/or LPAM-1 antagonists. They are described in International Patent Publications Nos. WO96/22966, WO98/53817, WO01/14328, WO99/06431, WO99/06432, WO99/06436, WO99/10312, WO99/48879, WO00/18759, WO00/20396, WO99/36393, WO99/52898, WO99/62901, WO00/67746 and WO02/08206. Those compounds described in these Publications have a urea structure or phenylalanine structure and do not have any 2-phenyl-3-heteroarylpropionic acid structure of the present invention. All conventional compounds also have problems that they lack bioavailability in oral administration and are easily decomposed in vivo. There is therefore required a compound that has properties desirable for therapeutical treatment and prophylaxis and which exhibits an antagonistic function against VLA-4 and/or LPAM-1.

DISCLOSURE OF THE INVENTION

The present invention has been made for therapeutical treatment and prophylaxis of the above diseases mediated by VLA-4 and LPAM-1. It is an object of the present invention to provide a novel 2-phenyl-3-heteroarylpropionic acid derivative as a compound that is excellent in oral absorption and an pharmacokinetics and which exhibits a VLA-4 and/or LPAM-1 antagonistic function or a salt thereof.

It is also another object of the present invention to provide a VLA-4 and/or LPAM-1 antagonist useful for the therapeutical treatment and prophylaxis of diseases mediated by VLA-4 and/or LPAM-1 and a pharmaceutical agent.

For achieving the above object, the present inventors have made diligent studies and as a result have found that a 2-phenyl-3-heteroarylpropionic acid derivative has excellent inhibitory effect against α4 integrin, and the present invention has been accordingly completed.

That is, the present invention provides (1) a 2-phenyl-3-heteroarylpropionic acid derivative of the general formula (I),

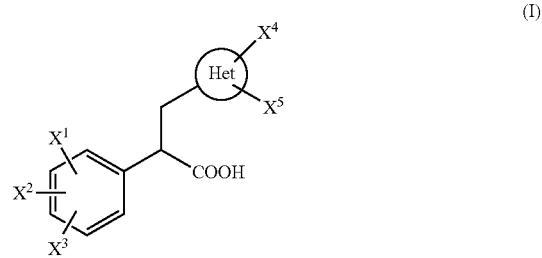

wherein Het is an aromatic heterocyclic ring and each of $X^1$ to $X^5$ is independently a hydrogen atom, a substituent having no organic group, a hydrocarbon or heteroaryl group that bonds to the benzene ring or the aromatic heterocyclic ring directly or through an oxygen atom, a sulfur atom, an oxycarbonyl group, a carbonyl group, a carbonyloxy group, a sulfonyl group or a sulfinyl group, —$NR^1R^2$, —$N(R^1)COR^2$, —$N(R^1)SO_2R^2$, —$N(R^1)CONR^2R^3$, —$OCONR^1R^2$ or —$CONR^1R^2$, (in which each of $R^1$, $R^2$ and $R^3$ is independently a hydrogen atom or a hydrocarbon or heteroaryl group which may have an oxygen atom at a terminal bonding site, and $R^1$ and $R^2$ may bond, or $R^2$ and $R^3$ may bond, to each other and form a ring that may contain a hetero atom, a double bond or a substituent,) provided that when two substituents of $X^1$, $X^2$ and $X^3$ bond to adjacent carbon atoms, the two substituents may bond to each other and form a benzene ring or a methylenedioxy group, or a salt thereof, (2) a 2-phenyl-3-heteroarylpropionic acid derivative or a salt thereof as recited in the above (1), wherein at least one of $X^4$ and $X^5$ in the general formula (I) is a group represented by any one of the general formulae (II) to (V),

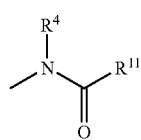  (II)

  (III)

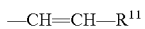  (IV)

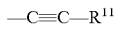  (V)

wherein $R^4$ is a hydrogen atom or an alkyl group having 1 to 15 carbon atoms and $R^{11}$ is a group represented by the general formula (VI) or (VII),

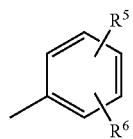  (VI)

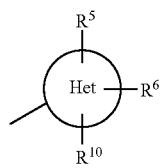  (VII)

wherein each of $R^5$ and $R^6$ is independently a hydrogen atom, a substituent having no organic group or a hydrocarbon or heteroaryl group that bonds to the benzene ring or the aromatic heterocyclic ring directly or through an oxygen atom, a sulfur atom, an oxycarbonyl group, a carbonyl group, a carbonyloxy group, a sulfonyl group or a sulfinyl group, —$NR^7R^8$, —$N(R^7)COR^8$, —$N(R^7)SO_2R^8$, —$N(R^7)CONR^8R^9$ or —$CONR^7R^8$, in which each of $R^7$, $R^8$ and $R^9$ is independently a hydrogen atom or a hydrocarbon or heteroaryl group which may have an oxygen atom at a terminal bonding site, and $R^7$ and $R^8$ may bond, or $R^8$ and $R^9$ may bond, to each other and form a ring that may contain a hetero atom, a double bond or a substituent, Het is an aromatic heterocyclic ring and $R^{10}$ is a hydrogen atom or an alkyl group having 1 to 15 carbon atoms, (3) a 2-phenyl-3-heteroarylpropionic acid derivative or a salt thereof as recited in the above (1) or (2), wherein at least one of $X^1$, $X^2$ and $X^3$ in the general formula (I) is —$NR^1R^2$, —$N(R^1)COR^2$, —$N(R^1)SO_2R^2$, —$N(R^1)CONR^2R^3$, an alkyl group, an alkoxy group, an aryl group, a heteroaryl group, an alkoxycarbonyl group, a halogen atom, a cyano group or an alkylthio group, (4) a 2-phenyl-3-heteroarylpropionic acid derivative or a salt thereof as recited in the above (3), wherein at least one of $X^1$, $X^2$ and $X^3$ is —$N(R^1) COR^2$ substituted on the 3-position, (5) a pharmaceutical agent containing, as an active ingredient, a 2-phenyl-3-heteroarylpropionic acid derivative or a salt thereof as recited in any one of the above (1) to (4), (6) a therapeutic or prophylactic pharmaceutical agent for an inflammatory patient having a disease state in which a cell adhesion process takes part, which pharmaceutical agent contains, as an active ingredient, a 2-phenyl-3-heteroarylpropionic acid derivative or a salt thereof as recited in any one of the above (1) to (4), (7) a therapeutic or prophylactic pharmaceutical agent for an inflammatory patient having a disease state in which a cell adhesion process caused by α4 integrin takes part, which pharmaceutical agent contains, as an active ingredient, a 2-phenyl-3-heteroarylpropionic acid derivative or a salt thereof as recited in any one of the above (1) to (4), (8) A therapeutic or prophylactic method for an inflammatory patient having a disease state in which a cell adhesion process takes part, which comprises administering a pharmaceutical agent containing, as an active ingredient, a 2-phenyl-3-heteroarylpropionic acid derivative or a salt thereof as recited in any one of the above (1) to (4), (9) A therapeutic or prophylactic method for an inflammatory patient having a disease state in which a cell adhesion process caused by α4 integrin takes part, which comprises administering a pharmaceutical agent containing, as an active ingredient, a 2-phenyl-3-heteroarylpropionic acid derivative or a salt thereof as recited in any one of the above (1) to (4),

(10) a cell adhesion inhibitor containing, as an active ingredient, a 2-phenyl-3-heteroarylpropionic acid derivative or a salt thereof as recited in any one of the above (1) to (4),

(11) an α4 integrin inhibitor containing, as an active ingredient, a 2-phenyl-3-heteroarylpropionic acid derivative or a salt thereof as recited in any one of the above (1) to (4),

(12) a VLA-4 antagonist containing, as an active ingredient, a 2-phenyl-3-heteroarylpropionic acid derivative or a salt thereof as recited in any one of the above (1) to (4), and

(13) a LPAM-1 antagonist containing, as an active ingredient, a 2-phenyl-3-heteroarylpropionic acid derivative or a salt thereof as recited in any one of the above (1) to (4).

PREFERRED EMBODIMENT OF THE INVENTION

In the present specification, it should be understood that the specified number of carbon atoms refers to the number of carbon atoms existing in the main portion of each group and does not include the number of carbon atoms existing in a substituent portion attached to said main portion. For example, in an alkyl group having an aryl group as a substituent (i.e., an arylalkyl group), any specified number of carbon atoms refers to the number of carbon atoms existing only in the alkyl portion constituting the arylalkyl group and does not include the number of carbon atoms of an aryl portion.

The 2-phenyl-3-heteroarylpropionic acid derivative or the salt thereof in the present invention is a compound having a structure of the general formula (I) or a salt thereof.

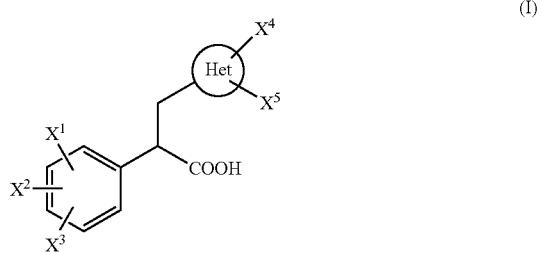

In the above general formula (I), Het is an aromatic heterocyclic ring, and each of $X^1$ to $X^5$ is independently a hydrogen atom, a substituent having no organic group, a hydrocarbon or heteroaryl group that bonds to the benzene ring or the aromatic heterocyclic ring directly or through an oxygen atom, a sulfur atom, an oxycarbonyl group, a carbonyl group, a carbonyloxy group, a sulfonyl group or a sulfinyl group, —$NR^1R^2$, —$N(R^1)COR^2$, —$N(R^1)SO_2R^2$, —$N(R^1)CONR^2R^3$, —$OCONR^1R^2$ or —$CONR^1R^2$.

The above aromatic heterocyclic ring represented by Het includes an aromatic heterocyclic ring containing 1 to 3 hetero atoms selected from nitrogen, oxygen and sulfur atoms. The above aromatic heterocyclic ring includes both a non-substituted aromatic heterocyclic ring and an aromatic heterocyclic ring having a substituent, and it further includes an aromatic heterocyclic ring having a structure formed of 2 or more rings that are fused (The term "aromatic heterocyclic ring" in the present specification is used in the above sense unless otherwise specified). Specific examples thereof include heterocyclic rings such as furan, thiophene, pyrrole, oxazole, thiazole, imidazole, triazole, tetrazole, pyridine, pyrimidine, indole, benzofuran, thianaphthene and purine.

Examples of the above substituent having no organic group include a halogen atom, a nitro group, a cyano group, a hydroxyl group and a carboxyl group. Specific examples of the halogen atom include a fluorine atom, a chlorine atom, a bromine atom and an iodine atom.

Examples of the above hydrocarbon or heteroaryl group that bonds to a benzene ring or the aromatic heterocyclic ring directly or through an oxygen atom, a sulfur atom, an oxycarbonyl group, a carbonyl group, a carbonyloxy group, a sulfonyl group or a sulfinyl group include an alkyl group having 1 to 15 carbon atoms, an alkenyl group having 2 to 15 carbon atoms, an alkynyl group having 2 to 15 carbon atoms, an aryl group having 6 to 10 carbon atoms, a heteroaryl group, an alkoxy group having 1 to 15 carbon atoms, an aryloxy group having 6 to 10 carbon atoms, a heteroaryloxy group, an alkoxycarbonyl group having 2 to 16 carbon atoms, an aryloxycarbonyl group having 7 to 11 carbon atoms, a heteroaryloxycarbonyl group, an alkylcarbonyl group having 2 to 16 carbon atoms, an arylcarbonyl group having 7 to 11 carbon atoms, a heteroarylcarbonyl group, an alkylcarbonyloxy group having 2 to 16 carbon atoms, an arylcarbonyloxy group having 7 to 11 carbon atoms, a heteroarylcarbonyloxy group, an alkylthio group having 1 to 15 carbon atoms, an arylthio group having 6 to 10 carbon atoms, a heteroarylthio group, an alkylsulfonyl group having 1 to 15 carbon atoms, an arylsulfonyl group having 6 to 10 carbon atoms, a heteroarylsulfonyl group, an alkylsulfinyl group having 1 to 15 carbon atoms, an arylsulfinyl group having 6 to 10 carbon atoms, a heteroarylsulfinyl group.

The above alkyl group having 1 to 15 carbon atoms includes both a non-substituted alkyl group and an alkyl group having a substituent, the alkyl chain thereof may be linear or branched, and further, the above alkyl group may be a cycloalkyl group having a structure of 1 or more cyclic rings and having 3 to 15 carbon atoms (in the present specification, the term "alkyl group" is used in the above sense unless otherwise specified). Specific examples of the non-substituted alkyl group having 1 to 15 carbon atoms include linear or branched alkyl groups such as methyl, ethyl, n-propyl, isopropyl, n-butyl, isobutyl, tert-butyl, sec-butyl, n-pentyl, tert-amyl, 3-methylbutyl, neopentyl, n-hexyl and n-decyl. Specific examples of the cycloalkyl group having 3 to 15 carbon atoms include cyclopropyl, cyclobutyl, cyclopentyl, cyclohexyl and cycloheptyl.

When the above alkyl group has a substituent, the substituent includes a halogen atom, a nitro group, a cyano group, a hydroxy group, a carboxyl group, an aryl group having 6 to 10 carbon atoms, a heteroaryl group, —OR, —SR, —SOR, $SO_2R$— and —NRR' (in the present specification, a substituent on the alkyl group portion of a substituent containing an alkyl group (e.g., an alkoxy group, an alkylthio group, etc.) similarly includes the above substituents unless otherwise specified). Each of the above R and R' is independently a hydrogen atom, an alkyl group having 1 to 10 carbon atoms, an alkenyl group having 2 to 10 carbon atoms, an aryl group having 6 to 10 carbon atoms or a heteroaryl group. When the above alkyl group is an alkyl group substituted with a halogen atom, i.e., a halogenated alkyl group, the halogenated alkyl group refers to a halogenated alkyl group having 1 to 15 carbon atoms, and specific examples thereof are trichloromethyl, trifluoromethyl, 1-chloroethyl and 2,2,2-trifluoroethyl. When the above alkyl group is an alkyl group substituted with an aryl group, the aryl group includes a monocyclic or bicyclic aryl group having 6 to 10 carbon atoms and containing no substituent or containing 1 to 3 substituents. Specific examples thereof include benzyl, 2-phenethyl, 1-phenethyl, 1-phenylpropyl, 1-naphthylmethyl and 2-naphthylmethyl. The aryl portion of the above arylalkyl group may have a substituent, and the substituent includes an alkyl group having 1 to 6 carbon atoms, an alkoxy group having 1 to 7 carbon atoms, a halogen atom, a nitro group, a cyano group, a hydroxyl group, a carboxyl group, an aryl group having 6 to 10 carbon atoms and an aryloxy group having 6 to 10 carbon atoms.

When the above alkyl group is an alkyl group substituted with a heteroaryl group, i.e., a heteroarylalkyl group, specific examples thereof include 2-pyridylmethyl, 3-furylmethyl and 2-(2-thienyl)ethyl. When the above alkyl group is an alkyl group substituted with an alkoxy group, i.e., an alkoxyalkyl group, the alkoxy group refers to an alkoxy group having 1 to 10 carbon atoms, and specific examples thereof include methoxymethyl, ethoxymethyl, isopropoxymethyl, 2-methoxyethyl and 1-methoxyisopropyl.

Further, the above alkyl group having a substituent includes alkyl groups represented by —$(CH_2)$—NRR', —$(CH_2)_n$—OR, —$(CH_2)_n$—SR, —$(CH_2)_n$—SOR and —$(CH_2)_n$—$SO_2R$. In this case, n is an integer of 1 to 3, R and R' are as defined above, and specific examples thereof are also as described above.

The above alkenyl group having 2 to 15 carbon atoms includes both a non-substituted alkenyl group and an alkenyl group having a substituent, the alkenyl chain thereof may be linear or branched, and further, the above alkenyl group may be a cycloalkenyl group having a structure of 1 or more cyclic rings (the term "alkenyl group" in the present specification will be used in this sense unless otherwise specified). When the above alkenyl group has a substituent, the substituent includes a halogen atom, a nitro group, a cyano group, a hydroxyl group, a carboxyl group, an aryl group having 6 to 10 carbon atoms, a heteroaryl group, —OR—, —SR, —SOR, —SO$_2$R and —NRR'. The above R and R' are as defined above. Specific examples of the above alkenyl group include vinyl, 1-propenyl, 2-propenyl, 2-methyl-1-propenyl and 1,2-dimethylpropenyl. Further, when the above alkenyl group is an alkenyl group substituted with an aryl group, i.e., an arylalkenyl group, the aryl group constituting the above arylalkenyl group is as defined with regard to the above aryl group, and specific examples thereof include 2-phenylvinyl, and the like. Further, the aryl portion of the above arylalkenyl group may have a substituent, and the substituent includes an alkyl group having 1 to 6 carbon atoms, an alkoxy group having 1 to 7 carbon atoms, a halogen atom, a nitro group, a cyano group, a hydroxy group, a carboxyl group, an aryl group having 6 to 10 carbon atoms and an aryloxy group having 6 to 10 carbon atoms.

The above alkynyl group having 2 to 15 carbon atoms includes both a non-substituted alkynyl group and an alkynyl group having a substituent, and the alkynyl chain thereof may be linear or branched (the term "alkynyl group" in the present specification will be used in this sense unless otherwise specified). When the above alkynyl group has a substituent, the substituent includes a halogen atom, a nitro group, a cyano group, a hydroxyl group, a carboxyl group, an aryl group having 6 to 10 carbon atoms, a heteroaryl group, —OR—, —SR, —SOR, —SO$_2$R and —NRR'. The above R and R' are as defined above. Specific examples of the above alkynyl group include hexynyl, phenylethynyl and pyridylethynyl. Further, when the above alkynyl is an alkynyl substituted with an aryl group, i.e., an arylalkynyl group, the aryl group constituting the above arylalkynyl group is as defined with regard to the above aryl group. The aryl portion of the above arylalkynyl group may further have a substituent, and the substituent includes an alkyl group having 1 to 6 carbon atoms, an alkoxy group having 1 to 7 carbon atoms, a halogen atom, a nitro group, a cyano group, a carboxyl group, a hydroxyl group, an aryl group having 6 to 10 carbon atoms and an aryloxy group having 6 to 10 carbon atoms.

The above aryl group having 6 to 10 carbon atoms includes both a non-substituted aryl group and an aryl group having a substituent (the term "aryl group" in the present specification will be used in this sense unless otherwise specified). Specific examples of the non-substituted aryl group having 6 to 10 carbon atoms include phenyl, 1-naphthyl and 2-naphthyl.

When the above aryl group has a substituent, the substituent includes an alkyl group having 1 to 10 carbon atoms, a halogen atom, a nitro group, a cyano group, a hydroxyl group, a carboxyl group, an aryl group having 6 to 10 carbon atoms, a heteroaryl group, —OR, —NRR'—, —SR, —SOR and —SO$_2$R (in the present specification, a substituent on the aryl group portion of a substituent containing an aryl group (e.g., an aryloxy group, an arylthio group, etc.) similarly includes the above substituents unless otherwise specified). R and R' are as defined above, and specific examples thereof are also as specified above. The aryl group having a substituent includes o-tolyl, 2,6-dimethoxyphenyl, 3-chlorophenyl, 2-cyanophenyl and biphenyl.

The above heteroaryl group refers to an aromatic heterocyclic ring group containing at least one hetero atom selected from 1 to 3 kinds of atoms such as nitrogen atoms, oxygen atoms and sulfur atoms, and the above heteroaryl group includes a non-substituted heteroaryl group and a heteroaryl group having a substituent (the term "heteroaryl group" in the present specification will be used in this sense unless otherwise specified). When the above heteroaryl group has a substituent, the substituent includes a halogen atom, a nitro group, a cyano group, a hydroxyl group, a carboxyl group, the above alkyl group, the above aryl group, —OR—, —NRR', —SR, —SOR and —SO$_2$R (in the present specification, a substituent on the aryl group portion of a substituent containing a heteroaryl group (e.g., a heteroaryloxy group, a heteroarylthio group, etc.) similarly includes the above substituents unless otherwise specified). R and R' are as defined above, and specific examples thereof are also as specified above. Specific examples of the above heteroaryl group include furyl, thienyl, imidazolyl, thiazolyl, oxazolyl, isooxazolyl, pyridyl, pyrazyl, indolyl, tetrazolyl and quinolyl.

The above alkoxy group having 1 to 15 carbon atoms includes both a non-substituted alkoxy group and an alkoxy group having a substituent, and the alkyl group constituting the alkoxy group is as defined with regard to the above alkyl group (the term "alkoxy group" in the present specification will be used in this sense unless otherwise specified). The substituent on the alkyl group portion thereof and specific examples thereof are also as described with regard to the above alkyl group. Specific examples of the non-substituted alkoxy group having 1 to 15 carbon atoms includes methoxy, ethoxy, n-propoxy, isopropoxy, n-butoxy, isobutoxy, tert-butoxy, sec-butoxy, n-pentyloxy, tert-amyloxy, neopentyloxy and n-hexyloxy.

When the above alkoxy group is an alkoxy group substituted with an alkoxy group, i.e., an alkoxyalkoxy group, specific examples thereof include methoxymethoxy and methoxyethoxymethoxy. When the above alkoxy group is an alkoxy group substituted with an aryl group, i.e., an arylalkoxy group, the aryl group as a substituent refers to an aryl group having 6 to 10 carbon atoms. Specific examples of the above arylalkoxy group include benzyloxy, 1-naphthylmethoxy, 2-naphthylmethoxy, 1-phenylethoxy, 4-methoxybenzyloxy, 2-phenylethoxy and 3-phenylpropoxy. When the above alkoxy group is an alkoxy group substituted with a heteroaryl group, i.e., a heteroarylalkoxy group, specific examples thereof include 2-pyridylmethoxy, (3,5-dichloropyrid-4-yl)methoxy and 2-(indol-1-yl)ethoxy.

The above aryloxy group having 6 to 10 carbon atoms includes both a non-substituted aryloxy group and an aryloxy group having a substituent, and the aryl group constituting the aryloxy group is as defined with regard to the above aryl group (the term "aryloxy group" in the present invention will be used in this sense unless otherwise specified). The substituent on the aryl group portion and specific examples thereof are also as described with regard to the above aryl group. Specific examples of the non-substituted aryloxy group having 6 to 10 carbon atoms include phenoxy and naphthoxy. Specific examples of the above aryloxy group having a substituent include 2-chlorophenoxy.

The above heteroaryloxy group includes both a non-substituted heteroaryloxy group and a heteroaryloxy group having a substituent, and the heteroaryl group constituting the heteroaryloxy group is as defined with regard to the above heteroaryl group (the term "heteroaryloxy group" in the present specification will be used in this sense unless otherwise specified). The substituent on the heteroaryl group portion and specific examples thereof are also as described with regard to the above heteroaryl group. Specific examples of the above heteroaryloxy group include 4-pyridyloxy and 2-pyrimidyloxy.

The above alkoxycarbonyl group having 2 to 16 carbon atoms includes both a non-substituted alkoxycarbonyl group and an alkoxycarbonyl group having a substituent, and the alkyl group constituting the alkoxycarbonyl group is as defined with regard to the above alkyl group (the term "alkoxycarbonyl group" in the present specification will be used in this sense unless otherwise specified). The substituent on the alkyl group portion and specific examples thereof are also as described with regard to the above alkyl group. Specific examples of the above alkoxycarbonyl group include methoxycarbonyl, ethoxycarbonyl, n-propoxycarbonyl, isopropoxycarbonyl, n-butoxycarbonyl, sec-butoxycarbonyl and tert-butoxycarbonyl.

The above aryloxycarbonyl group having 7 to 11 carbon atoms includes both a non-substituted aryloxycarbonyl group and an aryloxycarbonyl group having a substituent, and the aryl group constituting the aryloxycarbonyl group is as defined with regard to the above aryl group (the term "aryloxycarbonyl group" in the present specification will be used in this sense unless otherwise specified). The substituent on the aryl group portion and specific examples thereof are also as described with regard to the above aryl group. Specific examples of the above aryloxycarbonyl group include phenoxycarbonyl and naphthoxycarbonyl.

The above heteroaryloxycarbonyl group includes both a non-substituted heteroaryloxycarbonyl group and a heteroaryloxycarbonyl group having a substituent, and the heteroaryl group constituting the heteroaryloxycarbonyl group is as defined with regard to the above heteroaryl group (the term "heteroaryloxycarbonyl group" in the present specification will be used in this sense unless otherwise specified). The substituent on the heteroaryl group portion and specific examples thereof are also as described with regard to the above heteroaryl group above. Specific examples of the above heteroaryloxycarbonyl group include 4-pyridyloxycarbonyl.

The above alkylcarbonyl group having 2 to 16 carbon atoms include both a non-substituted alkylcarbonyl group and an alkylcarbonyl group having a substituent, and the alkyl group constituting the alkylcarbonyl group is as defined with regard to the above alkyl group (the term "alkylcarbonyl group" in the present specification will be used in this sense unless otherwise specified). The substituent on the alkyl group portion and specific examples thereof are as described with regard to the above alkyl group. Specific examples of the above alkylcarbonyl group include acetyl, propionyl, n-butanoyl and isobutanoyl.

The above arylcarbonyl group having 7 to 11 carbon atoms includes both a non-substituted arylcarbonyl group and an arylcarbonyl group having a substituent, and the aryl group constituting the arylcarbonyl group is as defined with regard to the above aryl group (the term "arylcarbonyl group" in the present specification will be used in this sense unless otherwise specified). The substituent on the aryl group portion and specific examples thereof are also as described with regard to the above aryl group. Specific examples of the above arylcarbonyl group include 3-chlorobenzoyl.

The above heteroarylcarbonyl group includes both a non-substituted heteroarylcarbonyl group and a heteroarylcarbonyl group having a substituent, and the heteroaryl group constituting the heteroarylcarbonyl group is as defined with regard to the above heteroaryl group (the term "heteroarylcarbonyl group" in the present specification will be used in this sense unless otherwise specified). The substituent on the heteroaryl group portion and specific examples thereof are also as described with regard to the above heteroaryl group. Specific examples of the above heteroarylcarbonyl group include 2-thiophenecarbonyl.

The above alkylcarbonyloxy group having 2 to 16 carbon atoms includes both a non-substituted alkylcarbonyloxy group and an alkylcarbonyloxy group having a substituent, and the alkyl group constituting the alkylcarbonyloxy group is as defined with regard to the above alkyl group (the term "alkylcarbonyloxy group" in the present specification will be used in this sense unless otherwise specified). The substituent on the alkyl group portion and specific examples thereof are also as described with regard to the above alkyl group. Specific examples of the above alkylcarbonyloxy group include acetoxy.

The above arylcarbonyloxy group having 7 to 11 carbon atoms includes both a non-substituted arylcarbonyloxy group and an arylcarbonyloxy group having a substituent, and the aryl group constituting the arylcarbonyloxy group is as defined with regard to the above aryl group (the term "arylcarbonyloxy group" in the present specification will be used in this sense unless otherwise specified). The substituent on the aryl group portion and specific examples thereof are also as described with regard to the above aryl group. Specific examples of the above arylcarbonyloxy group include benzoyloxy.

The above heteroarylcarbonyloxy group includes both a non-substituted heteroarylcarbonyloxy group and a heteroarylcarbonyloxy group having a substituent, and the heteroaryl group constituting the heteroarylcarbonyloxy group is as defined with regard to the above heteroaryl group (the term "heteroarylcarbonyloxy group" in the present specification will be used in this sense unless otherwise specified). The substituent on the heteroaryl group portion and specific examples thereof are also as described with regard to the above heteroaryl group. Specific examples of the above heteroarylcarbonyloxy group include 3-pyridinecaronyloxy.

The above alkylthio group having 1 to 15 carbon atoms includes both a non-substituted alkylthio group and an alkylthio group having a substituent, and the alkyl group constituting the alkylthio group is as defined with regard to the above alkyl group (the term "alkylthio group" in the present specification will be used in this sense unless otherwise specified). The substituent on the alkyl group portion and specific examples thereof are also as described with regard to the above alkyl group. Specific examples of the above alkylthio group include methylthio, ethylthio, n-propylthio, isopropylthio, n-butylthio, sec-butylthio and tert-butylthio.

The above arylthio group having 6 to 10 carbon atoms includes both a non-substituted arylthio group and an arylthio group having a substituent, and the aryl group constituting the arylthio group is as defined with regard to the above aryl group (the term "arylthio group" in the present specification will be used in this sense unless otherwise specified). The substituent on the aryl group portion and specific examples thereof are also as described with regard to the above aryl group. Specific examples of the above arylthio group include phenylthio and tolylthio.

The above heteroarylthio group includes both a non-substituted heteroarylthio group and a heteroarylthio group having a substituent, and the heteroaryl group constituting the heteroarylthio group is as defined with regard to the above heteroaryl group (the term "heteroarylthio group" in the present specification will be used in this sense unless otherwise specified). The substituent on the heteroaryl group portion and specific examples thereof are also as described with regard to the above heteroaryl group. Specific examples of the above heteroarylthio group include pyridylthio, imidazolidylthio and thienylthio.

The above alkylsulfonyl group having 1 to 15 carbon atoms includes both a non-substituted alkylsulfonyl group and an alkylsulfonyl group having a substituent, and the alkyl group constituting the alkylsulfonyl group is as defined with regard to the above alkyl group (the term "alkylsulfonyl group" in the present specification will be used in this sense unless otherwise specified). The substituent on the alkyl group portion and specific examples thereof are also as described with regard to the above alkyl group. Specific examples of the above alkylsulfonyl group include methanesulfonyl, ethanesulfonyl, n-propylsulfonyl, isopropylsulfonyl, n-butylsulfonyl, sec-butylsulfonyl and tert-butylsulfonyl.

The above arylsulfonyl group having 6 to 10 carbon atoms includes both a non-substituted arylsulfonyl group and an arylsulfonyl group having a substituent, and the aryl group constituting the arylsulfonyl group is as defined with regard to the above aryl group (the term "arylsulfonyl group" in the present specification will be used in this sense unless otherwise specified). The substituent on the aryl group portion and specific examples thereof are also as described with regard to the above aryl group. Specific examples of the above arylsulfonyl group include benzenesulfonyl, fluorobenzenesulfonyl and tosyl.

The above heteroarylsulfonyl group includes both a non-substituted heteroarylsulfonyl group and an heteroarylsulfonyl group having a substituent, and the heteroaryl group constituting the heteroarylsulfonyl group is as defined with regard to the above heteroaryl group (the term "heteroarylsulfonyl group" in the present specification will be used in this sense unless otherwise specified). The substituent on the heteroaryl group portion and specific examples thereof are also as described with regard to the above heteroaryl group. Specific examples of the above heteroarylsulfonyl group include 2-pyridylsulfonyl and 2-thienylsulfonyl.

The above alkylsulfinyl group having 1 to 15 carbon atoms includes both a non-substituted alkylsulfinyl group and an alkylsulfinyl group having a substituent, and the alkyl group constituting the alkylsulfinyl group is as defined with regard to the above alkyl group (the term "alkylsulfinyl group" in the present specification will be used in this sense unless otherwise specified). The substituent on the alkyl group portion and specific examples thereof are also as described with regard to the above alkyl group. Specific examples of the above alkylsulfinyl group include methanesulfinyl, ethanesulfinyl, n-propylsulfinyl, isopropylsulfinyl, n-butylsulfinyl, sec-butylsulfinyl and tert-butylsulfinyl.

The above arylsulfinyl group having 6 to 10 carbon atoms includes both a non-substituted arylsulfinyl group and an arylsulfinyl group having a substituent, and the aryl group constituting the arylsulfinyl group is as defined with regard to the above aryl group (the term "arylsulfinyl group" in the present specification will be used in this sense unless otherwise specified). The substituent on the aryl group portion and specific examples thereof are also as described with regard to the above aryl group. Specific examples of the above arylsulfinyl group include benzenesulfinyl.

The above heteroarylsulfinyl group includes both a non-substituted heteroarylsulfinyl group and a heteroarylsulfinyl group having a substituent, and the heteroaryl group constituting the heteroarylsulfinyl group is as defined with regard to the above heteroaryl group (the term "heteroarylsulfinyl group" in the present specification will be used in this sense unless otherwise specified). The substituent on the heteroaryl group portion and specific examples thereof are also as described with regard to the above heteroaryl group. Specific examples of the above heteroarylsulfinyl group include 2-pyridylsulfinyl and 2-thienylsulfinyl.

In the above $-NR^1R^2$, $-N(R^1)COR^2$, $-N(R^1)SO_2R^2$, $-N(R^1)CONR^2R^3$, $-OCONR^1R^2$ and $-CONR^1R^2$, each of $R^1$, $R^2$ and $R^3$ is independently a hydrogen atom or a hydrocarbon or heteroaryl group that may have an oxygen atom at a terminal bonding site. Examples of the hydrocarbon or heteroaryl group that may have an oxygen atom at a terminal bonding site include an alkyl group having 1 to 15 carbon atoms, an alkenyl group having 2 to 15 carbon atoms, an alkoxy group having 1 to 15 carbon atoms, an aryl group having 6 to 10 carbon atoms, an aryloxy group having 6 to 10 carbon atoms, a heteroaryl group and a heteroaryloxy group. These groups are as defined above, and specific examples thereof are also as described above.

$R^1$ and $R^2$ may bond to each other, or $R^2$ and $R^3$ may bond to each other, and form a ring that may have a hetero atom, a double bond or a substituent. The above hetero atom is at least one atom selected from oxygen atoms, nitrogen atoms and sulfur atoms. The ring that is formed includes lactam, pyrrolidine, piperidine, morpholine and hydantoin. When the ring that is formed has a substituent, the substituent includes those represented by each of the above $X^1$ to $X^5$.

When two members of $X^1$, $X^2$ and $X^3$ bond to adjacent two carbon atoms, the two members may bond to each other and form a benzene ring or a methylenedioxy group.

The compound of the above general formula (I) preferably includes a compound of the general formula (I) wherein at least one of $X^4$ and $X^5$ is a group represented by any one of the following general formula (II) to (V),

(II)

(III)

(IV)

(V)

in which $R^4$ is a hydrogen atom or an alkyl group having 1 to 15 carbon atoms and $R^{11}$ is a group of the general formula (VI) or (VII).

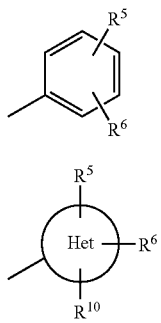

In the above general formulae (VI) and (VII), each of $R^5$ and $R^6$ is independently a hydrogen atom, a substituent having no organic group, a hydrocarbon or heteroaryl group that bonds to a benzene ring or an aromatic heterocyclic ring directly or through an oxygen atom, a sulfur atom, an oxycarbonyl group, a carbonyl group, a carbonyloxy group, a sulfonyl group or a sulfinyl group, $-NR^7R^8$, $-N(R^7)COR^8$, $-N(R^7)SO_2R^8$, $-N(R^7)CONR^8R^9$ or $-CONR^7R^8$. In the above formulae, further, Het is an aromatic heterocyclic ring and $R^{10}$ is a hydrogen atom or an alkyl group having 1 to 15 carbon atoms.

Examples of the substituent having no organic group, represented by each of the above $R^5$ and $R^6$, include a halogen atom, a nitro group, a cyano group, a hydroxyl group and a carboxyl group. Examples of the hydrocarbon or heteroaryl group that bonds to the benzene ring or the aromatic heterocyclic ring directly or through an oxygen atom, a sulfur atom, an oxycarbonyl group, a carbonyl group, a carbonyloxy group, a sulfonyl group or a sulfinyl group include an alkyl group having 1 to 15 carbon atoms, an alkenyl group having 2 to 15 carbon atoms, an alkynyl group having 2 to 15 carbon atoms, an aryl group having 6 to 10 carbon atoms, a heteroaryl group, an alkoxy group having 1 to 15 carbon atoms, an aryloxy group having 6 to 10 carbon atoms, a heteroaryloxy group, an alkoxycarbonyl group having 2 to 16 carbon atoms, an aryloxycarbonyl group having 7 to 11 carbon atoms, a heteroaryloxycarbonyl group, an alkylcarbonyl group having 2 to 16 carbon atoms, an arylcarbonyl group having 7 to 11 carbon atoms, a heteroarylcarbonyl group, an alkylcarbonyloxy group having 2 to 16 carbon atoms, an arylcarbonyloxy group having 7 to 11 carbon atoms, a heteroarylcarbonyloxy group, an alkylthio group having 1 to 15 carbon atoms, an arylthio group having 6 to 10 carbon atoms, a heteroarylthio group, an alkylsulfonyl group having 1 to 15 carbon atoms, an arylsulfonyl group having 6 to 10 carbon atoms, a heteroarylsulfonyl group, an alkylsulfinyl group having 1 to 15 carbon atoms, an arylsulfinyl group having 6 to 10 carbon atoms and a heteroarylsulfinyl group.

The alkyl group represented by each of $R^4$, $R^5$, $R^6$ and $R^{10}$ is as defined with regard to the already explained alkyl group, and specific examples thereof are also as described with regard to the already explained alkyl group. The halogen atom, aryl group, alkoxy group, aryloxy group, heteroaryloxy group, alkoxycarbonyl group, alkylcarbonyl group, arylcarbonyl group, heteroarylcarbonyl group, alkylcarbonyloxy group, arylcarbonyloxy group, heteroarylcarbonyloxy group, alkylthio group, arylthio group, heteroarylthio group, alkylsulfonyl group, arylsulfonyl group, heteroarylsulfonyl group, alkylsulfinyl group, arylsulfinyl group and heteroarylsulfinyl group represented by each of $R^5$ and $R^6$ are as defined with regard to the already explained corresponding groups, and specific examples thereof are also as described with regard to the already explained corresponding groups.

In the above $-NR^7R^8$, $-N(R^7)COR^8$, $-N(R^7)SO_2R^8$, $-N(R^7)CONR^8R^9$ and $-CONR^7R^8$, each of $R^7$, $R^8$ and $R^9$ is independently a hydrogen atom or a hydrocarbon or heteroaryl group that may have an oxygen atom at a terminal bonding site. Examples of the hydrocarbon or heteroaryl group that may have an oxygen atom at a terminal bonding site include an alkyl group having 1 to 15 carbon atoms, an alkenyl group having 2 to 15 carbon atoms, an alkoxy group having 1 to 15 carbon atoms, an aryl group having 6 to 10 carbon atoms, an aryloxy group having 6 to 10 carbon atoms, a heteroaryl group and a heteroaryloxy group. These groups are as defined with regard to the already explained corresponding groups, and specific examples thereof are also as described with regard to the already explained corresponding groups.

Further, $R^7$ and $R^8$ may bond, or $R^8$ and $R^9$ may bond, to each other and form a ring that may contain a hetero atom, a double bond or a substituent. The above ring is also as explained with regard to the above $R^1$ and $R^2$ or the above $R^2$ and $R^3$.

Further, the compound of the above general formula (I) is preferably a compound of the general formula (I) wherein at least one of $X^1$, $X^2$ and $X^3$ is $-NR^1R^2$, $-N(R^1)COR^2$, $-N(R^1)SO_2R_2$, $-N(R^1)CONR^2R^3$, an alkyl group, an alkoxy group, an aryl group, a heteroaryl group, an alkoxycarbonyl group, a halogen atom, a cyano group or an alkylthio, and particularly preferably a compound of the general formula (I) wherein at least one of $X^1$, $X^2$ and $X^3$ is $-N(R^1)COR^2$ substituted on the 3-position.

When the compound of the above general formula (I), provided by the present invention, has an asymmetric carbon, the compound of the present invention includes a racemate thereof, a diastereo isomer thereof and individual optically active compounds thereof. When geometrical isomers exist, the present invention also includes (E)- and (Z)-configuration compounds and a mixture of these.

The salt of the compound of the above general formula (I), provided by the present invention, is not specially limited so long as it is a pharmaceutically acceptable salt. Examples of the salt include a salt with an inorganic base, a salt with an organic base, a salt with an organic acid, a salt with an inorganic acid and a salt with an amino acid. Examples of the salt with an inorganic base include alkali metal salts such as a sodium salt, a potassium salt and a calcium salt and an ammonium salt. Examples of the salt with an organic base include a triethylamine salt, a pyridine salt, an ethanolamine salt, a cyclohexylamine salt and a dicyclohexylamine salt. Examples of the salt with an organic acid include a formate, an acetate, a tartarate, a maleate, a succinate and a methanesulfonate. Examples of the salt with an inorganic acid include a hydrochloride, a hydrobromate and a nitrate. Examples of the salt with an amino acid include a glycine salt, an alanine salt, an arginine salt, a glutamate and an aspartate.

The compound of the general formula (I), provided by the present invention, can be produced by the following preparation method A.

Preparation method A:

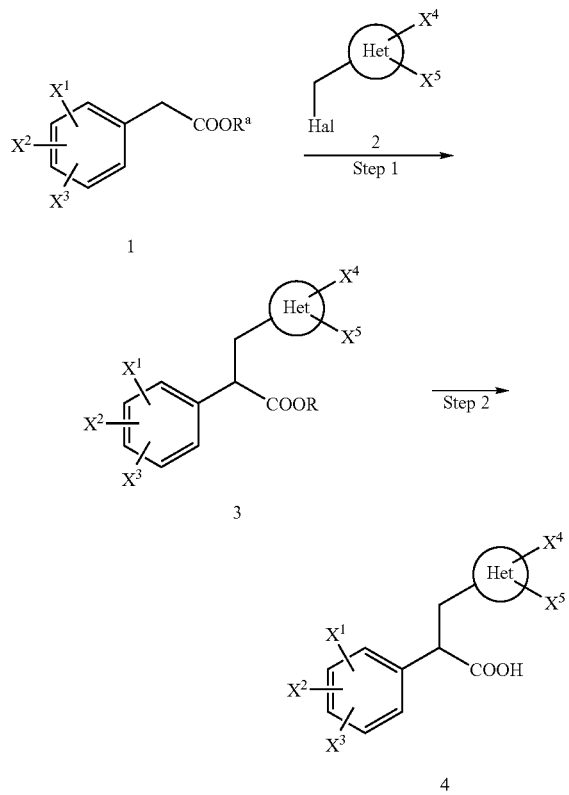

wherein $X^1$ to $X^5$ and Het are as defined in the above general formula (I), $R^a$ is an alkyl group having 1 to 15 carbon atoms, and Hal is a halogen atom.

(Step 1)

A phenyl acetate derivative of the general formula 1 is reacted with a base such as lithium diisopropylamide in a proper neutral solvent (such as tetrahydrofuran) at a low temperature to generate an enolate anion, and then the enolate anion is reacted with a halide of the general formula 2, whereby a corresponding compound of the general formula 3 can be prepared.

(Step 2)

The alkyl ester derivative of the general formula 3 is decomposed with an aqueous solution of an alkali such as lithium hydroxide, sodium hydroxide or potassium hydroxide under an alkaline condition, whereby a compound of the general formula 4 can be prepared. While any reaction solvent can be used without any limitation so long as it is miscible with water, the solvent is preferably selected from methanol, ethanol, tetrahydrofuran, 1,4-dioxane or dimethoxyethane. The reaction temperature is not critical, and the reaction is generally carried out at 0 to 100° C. The reaction time period is preferably 30 minutes to 6 hours.

The compound of the general formula (2) for use in the above step 1, when it is a picolyl halide, can be synthesized according to the following preparation method B.

Preparation method B:

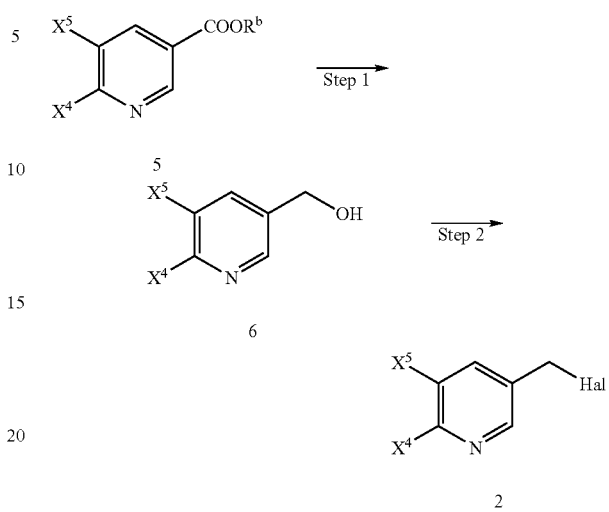

wherein each of $X^4$, $X^5$ and Hal are as defined above, and $R^b$ is an alkyl group having 1 to 15 carbon atoms.

(Step 1)

An ethyl nicotinate derivative of the general formula 5 is reacted with a reducing agent such as lithium aluminum hydride in a proper neutral solvent (such as tetrahydrofuran), whereby a corresponding compound of the general formula 6 can be prepared.

(Step 2)

A hydroxyl group on the compound of the general formula 6 can be replaced with a chlorine atom, a bromine atom or an iodine atom according to a method well known and recognized in the field of this art. For example, the compound of the general formula 6 is reacted with triphenylphosphine and carbon tetrabromide in dichloromethane, whereby the above hydroxyl group can be replaced with a bromide. While any reaction solvent can be used without any limitation so long as it does not greatly impair the reaction, the solvent is preferably selected from dichloromethane, chloroform or 1,2-dichloroethane.

The compound of the present invention, prepared by the above method, is isolated and purified in the form of a free compound, a salt thereof, any one of various solvents thereof (e.g., hydrate, ethanol solvate or the like) or a crystal polymorph substance. When the compound of the present invention is a salt, a pharmaceutically acceptable salt can be prepared according to a conventional salt-forming reaction. The isolation and purification are carried out by chemical procedures such as extraction, crystallization, fractionation chromatography of various types, or the like. An optical isomer can be obtained by asymmetric synthesis or by selecting proper starting compounds, or the compound of the present invention can be obtained as a stereo-chemically pure isomer by optical resolution of a racemic compound.

Tables 1 to 4 show examples of the substituents on the compound of the general formula (I), provided by the present invention. After Table 4, there are illustrated structural formulae of examples of compounds of types different from the type of the compounds shown in Tables 1 to 4.

TABLE 1

[Structure: core scaffold with pyridine ring (positions 1'-6') connected via CH2 to a benzene ring (positions 1-6) bearing X1, X2, X3 substituents and a CH(COOH) group; pyridine bears X4, X5 substituents]

| Compound No. | X¹ | X² | X³ | X⁴ | X⁵ |
|---|---|---|---|---|---|
| 1 | [iBu-N(Me)-C(=O)-CH(Me)2] (3-) | MeO— (4-) | H | [2,6-dichloro-N-methylbenzamide] (6'-) | H |
| 2 | [iBu-N(Me)-C(=O)-C(Me)3] (3-) | MeO— (4-) | H | [2,6-dichloro-N-methylbenzamide] (6'-) | H |
| 3 | [iBu-N(Me)-C(=O)-C(Me)3] (3-) | MeO— (4-) | H | [3,5-dichloro-N-methylpyridine-4-carboxamide] (6'-) | H |
| 4 | [iBu-N(Me)-C(=O)-CH(Et)(CH2Me)] (3-) | MeO— (4-) | H | [2,6-dichloro-N-methylbenzamide] (6'-) | H |
| 5 | [iBu-N(Me)-C(=O)-O-CH2-Ph] (3-) | MeO— (4-) | H | [2,6-dichloro-N-methylbenzamide] (6'-) | H |
| 6 | [iBu-N(Me)-C(=O)-CH(Me)2] (3-) | EtO— (4-) | H | [2,6-dichloro-N-methylbenzamide] (6'-) | H |

TABLE 1-continued

[Structure: 2-phenyl-3-(pyridin-3-yl)propanoic acid core with substituents X¹, X², X³ on phenyl ring and X⁴, X⁵ on pyridine ring]

| Compound No. | X¹ | X² | X³ | X⁴ | X⁵ |
|---|---|---|---|---|---|
| 7 | Me-N(iBu)-C(O)-C(Me)₂-Me (3-) | EtO— (4-) | H | 2,6-dichloro-N-methylbenzamide (6'-) | H |

TABLE 2

[Structure: 2-phenyl-3-(pyridin-3-yl)propanoic acid core with substituents X¹, X², X³ on phenyl ring and X⁴, X⁵ on pyridine ring]

| Compound No. | X¹ | X² | X³ | X⁴ | X⁵ |
|---|---|---|---|---|---|
| 8 | Me-N(iBu)-C(O)-C(Me)₂-Me (3-) | EtO— (4-) | H | 3,5-dichloro-N-methylpyridine-4-carboxamide (6'-) | H |
| 9 | Me-N(iBu)-C(O)-CH(Et)₂ (3-) | EtO— (4-) | H | 2,6-dichloro-N-methylbenzamide (6'-) | H |

TABLE 2-continued

| Compound No. | X¹ | X² | X³ | X⁴ | X⁵ |
| --- | --- | --- | --- | --- | --- |
| 10 | N-methyl-N-isobutyl benzyloxycarbamate (3-) | EtO— (4-) | H | 2,6-dichloro-N-methylbenzamide (6'-) | H |
| 11 | N-isobutyl-N,2,2-trimethylpropanamide (3-) | H | H | 2,6-dichloro-N-methylbenzamide (6'-) | H |
| 12 | 2-ethyl-N-isobutyl-N-methylbutanamide (3-) | H | H | 2,6-dichloro-N-methylbenzamide (6'-) | H |
| 13 | N-isobutyl-N,2,2-trimethylpropanamide (3-) | 1-methoxypropyl (4-) | H | 2,6-dichloro-N-methylbenzamide (6'-) | H |
| 14 | N-isobutyl-N,2,2-trimethylpropanamide (3-) | 1-methoxypropyl (4-) | H | 3,5-dichloro-N-methylpyridine-4-carboxamide (6'-) | H |

TABLE 3

| Compound No. | X¹ | X² | X³ | X⁴ | X⁵ |
|---|---|---|---|---|---|
| 15 | 3-: N-isobutyl-N-methyl-2-ethylbutanamide | 4-: MeOCH₂CH(Me)- | H | 6'-: 2,6-dichloro-N-methylbenzamide | H |
| 16 | 3-: N-isobutyl-N-methyl-pivalamide | 4-: MeOCH(Me)- | H | 6'-: 2,6-dichloro-N-methylbenzamide | H |
| 17 | 3-: N-isobutyl-N-methyl-pivalamide | 4-: Et— | H | 6'-: 2,6-dichloro-N-methylbenzamide | H |
| 18 | 3-: N-isobutyl-N-methyl-pivalamide | 4-: Et— | H | 6'-: 3,5-dichloro-N-methylpyridine-4-carboxamide | H |
| 19 | 3-: N-isobutyl-N-methyl-pivalamide | 5-: F₃C— | H | 6'-: 2,6-dichloro-N-methylbenzamide | H |
| 20 | 3-: N-isobutyl-N-methyl-pivalamide | 4-: MeO— | H | 6'-: 2,6-dimethoxy-3-methylphenyl | H |

TABLE 3-continued
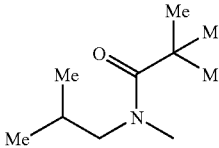
| Compound No. | X¹ | X² | X³ | X⁴ | X⁵ |
|---|---|---|---|---|---|
| 21 | 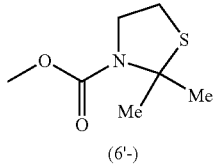 (3-) | MeO— (4-) | H | 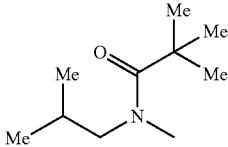 (6'-) | H |
TABLE 4
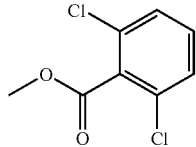
| Compound No. | X¹ | X² | X³ | X⁴ | X⁵ |
|---|---|---|---|---|---|
| 22 | 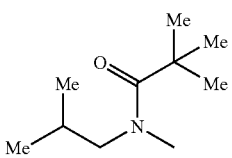 (3-) | MeO— (4-) | H | 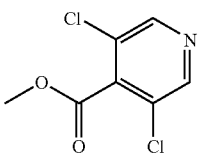 (6'-) | H |
| 23 | 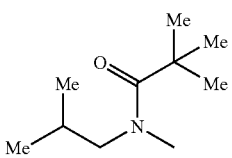 (3-) | MeO— (4-) | H | 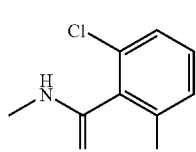 (6'-) | H |
| 24 | MeO— (2-) | MeO— (5-) | H | 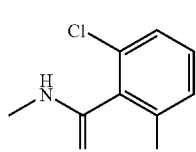 (6'-) | H |

TABLE 4-continued
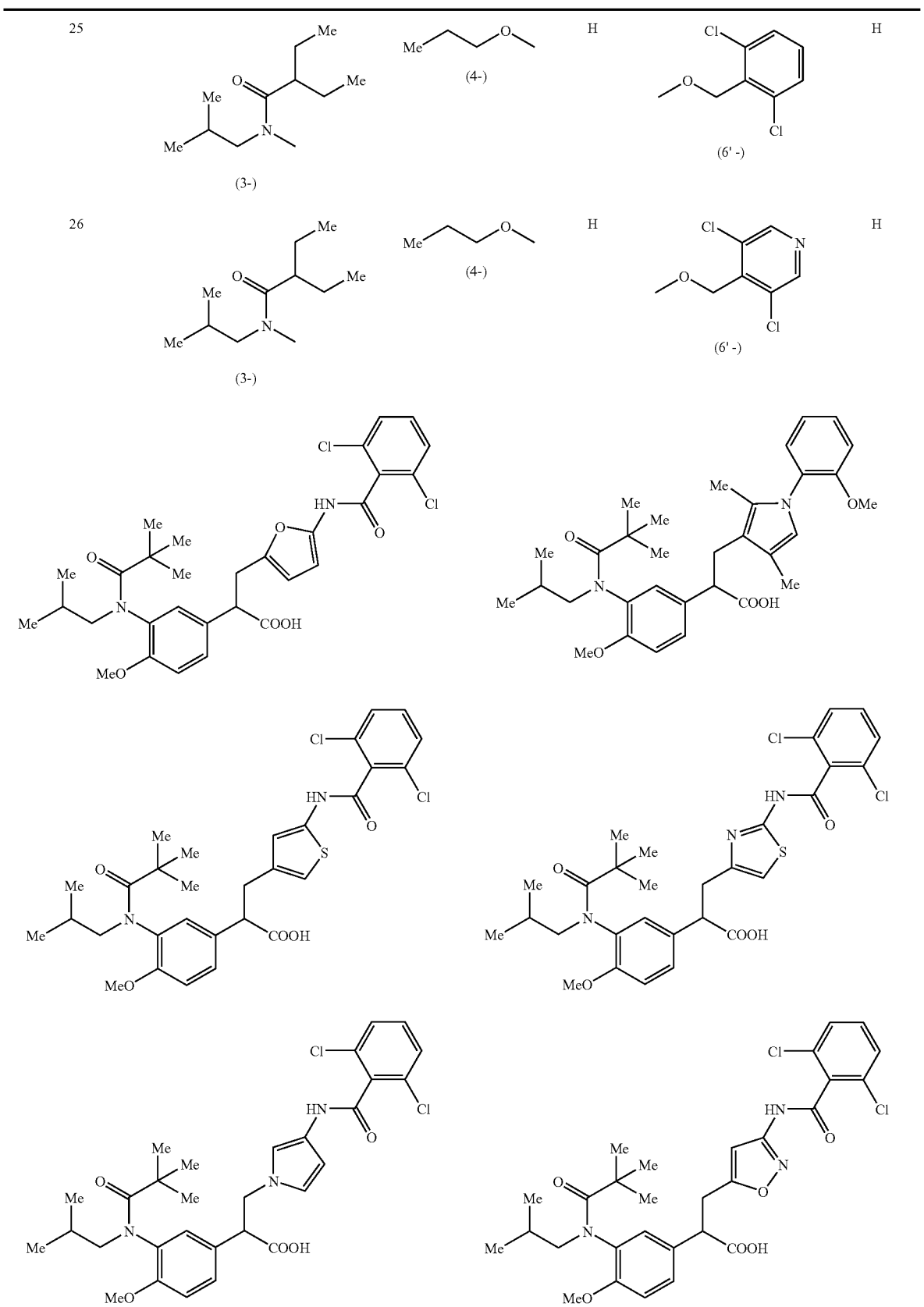

TABLE 4-continued

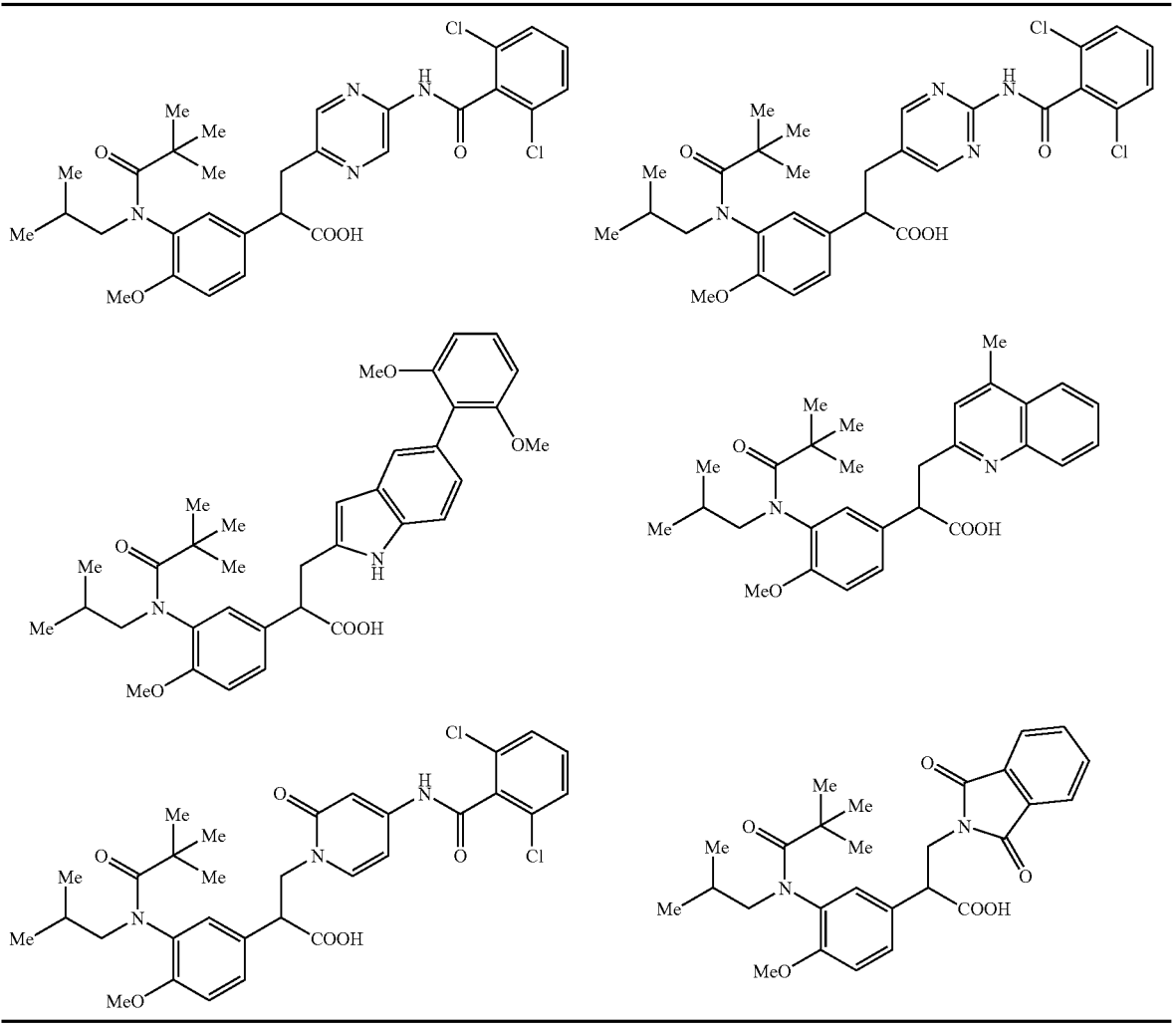

In Tables, Me represents methyl and Et represents ethyl.

The 2-phenyl-3-heteroarylpropionic acid derivative and its salt, provided by the present invention, exhibit excellent VLA-4 and/or LPAM-1 antagonistic action and are useful as a therapeutic or prophlactic pharmaceutical agent against diseases caused by adhesion and infiltration of leucocyte or diseases in which VLA-4 and/or LPAM-1-dependent adhesion process plays some role. The above diseases include autoimmune diseases such as rheumaticoid arthritis, systemic lupus erythematosus, multiple sclerosis and Sjögren's syndrome, various organ inflammations caused together with theses, allergic diseases such as asthma, atopic dermatitis, congested nose and rhinitis, inflammatory bowel diseases including Crohn's disease, nephritis, hepatitis, inflammatory diseases of central nerve system, cardiovascular disease, arteriosclerosis, diabetes and various malignant tumors. It is also used preventing damage of transplant organ, and blocking of proliferation and metastasis of tumor.

The compound of the present invention is systemically or topically administered by any one of methods such as an oral method, an intravenous injection method, a hypodermic injection method, an intra-rectum administration method and the like. Of these, oral administration is desirable. Further, the dosage form can be selected as required depending upon an administration route and includes, for example, a tablet, a troche, a sublingual tablet, a sugar-coated tablet, a capsule, a ball, powdered medicine, granules, liquid medicine, an emulsifiable concentrate, a syrup, a respiratory tonic, an ophthalmic solution, a collunarium, an injectable solution and a suppository. Further, these preparations can be produced by incorporating a diluting agent, an antiseptic agent, a wetting agent, an emulsifier, a stabilizer and a solubilizing agent.

The dose of the compound of the present invention can be determined as required depending upon conditions such as an administration route, a patient to whom it is to be administered, a symptom and the like. For example, when it is administered to an adult patient, the dose, or an amount at one time, of the compound of the present invention as an active ingredient is in the range of approximately 0.1 to 100 mg/kg, preferably 1 to 30 mg/kg, and preferably, it is administered once to three times a day.

EXAMPLES

The present invention will be explained with reference to Examples hereinafter, while the present invention shall not be limited by these Examples.

In ¹H-NMR spectrum measured in Examples below, tetramethylsilane (TMS) was used as an internal standard, the measurement was made with a JNM-EX270 model spectrometer (270 MHz, manufactured by JEOL Ltd.), and δ values were shown by ppm. Coupling constants (J) were shown by Hz, and in the resolution mode, the following abbreviations were used. s=singlet, d=doublet, t=triplet, q=quartet, m=multiplet, br=broad. For measurement of low-resolution mass spectrum (FABMS), a JMS-HX-110A model manufactured by JEOL Ltd. was used.

In the following general formulae and Tables, Me represents methyl, and Et represents ethyl.

Example 1

Preparation of 3-[2-(2,6-dichlorobenzoylamino)pyrid-5-yl]-2-{3-[(2,2-dimethylpropionyl)isobutylamino]-4-methoxyphenyl}propionic acid A compound (I-a) having the following structure was prepared according to the following reaction scheme.

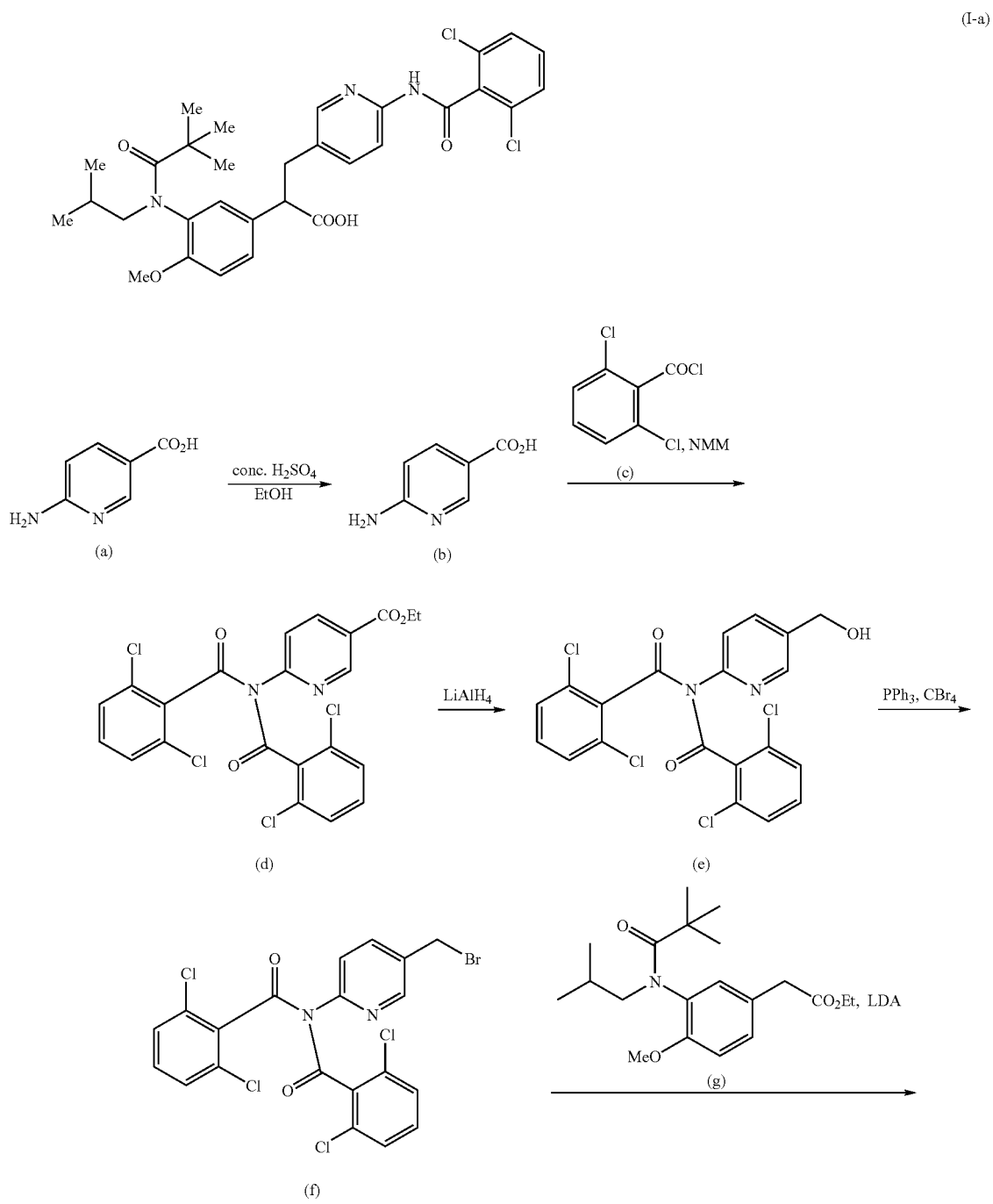

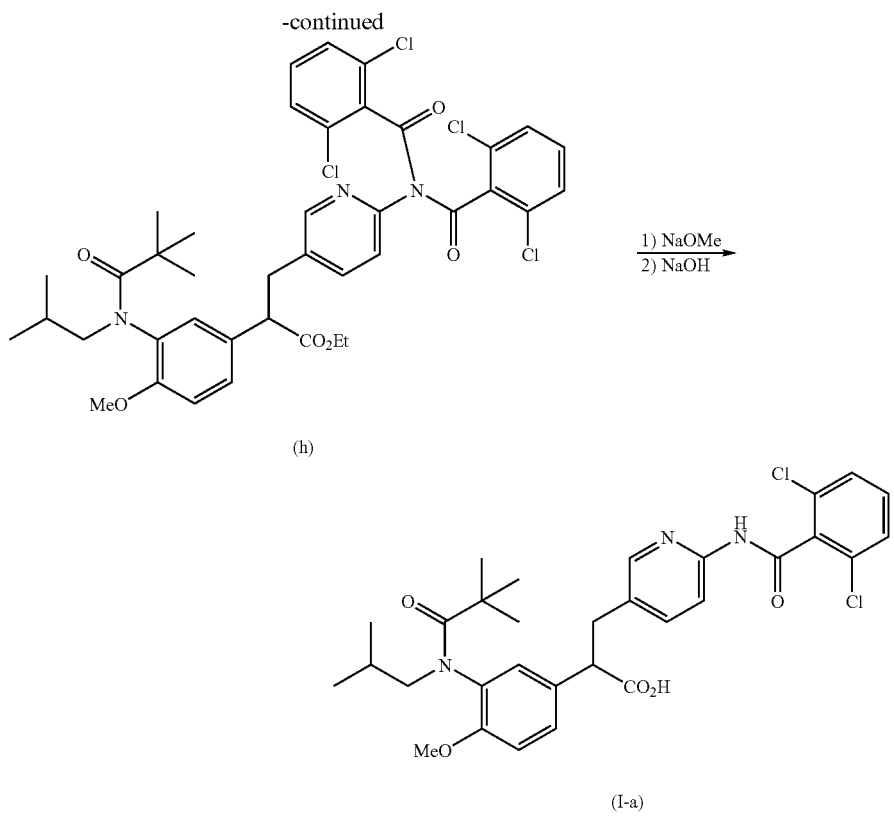

wherein NMM is N-methylmorpholine and LDA is lithiumdiisopropylamide.

11.5 Grams (83 mmol) of 6-aminonicotinic acid (a) was dissolved in 85 ml of ethanol, 2.5 ml of concentrated sulfuric acid was added, and the mixture was refluxed under heat for 24 hours. The solvent was removed under vacuum, 150 ml of ice water was poured, and a saturated sodium hydrogen carbonate aqueous solution was added. The mixture was subjected to extraction with ethyl acetate, the extract was dried over anhydrous magnesium sulfate, and the solvent was evaporated off under vacuum to give 10.0 g (yield 73%) of ethyl 6-aminonicotinate ester (b) in the form of a white solid.

10.0 Grams (60 mmol) of ethyl 6-aminonicotinate ester (b) was dissolved in 150 ml of dichloromethane, and 9.2 ml (84 mmol) of N-methylmorpholine was added. At 0° C., 9.5 ml (66 mmol) of 2,6-dichlorobenzoyl chloride (c) was added, and the mixture was stirred at room temperature for 24 hours.

Further, 9.2 ml (84 mmol) of N-methylmorpholine and 9.5 ml (66 mmol) of 2,6-dichlorobenzoyl chloride (c) were added, and the mixture was stirred for 4 days. Water was added, and the solvent was removed under vacuum.

Water was added, the mixture was subjected to extraction with ethyl acetate, and the extract was dried over anhydrous magnesium sulfate. The solvent was evaporated off under vacuum, and the residue was purified by silica gel column chromatography (chloroform:methanol (volume ratio)=400:1-200:1), to give 14.0 g (yield 45%) of ethyl N,N-bis(2,6-dichlorobenzoyl)-6-aminonicotinate ester (d).

14.0 Grams (27 mmol) of ethyl N,N-bis(2,6-dichlorobenzoyl)-6-aminonicotinate ester (d) was dissolved in 200 ml of tetrahydrofuran. At 0° C., a solution of 21 g (55 mmol) of lithium aluminum hydride in 200 ml of tetrahydrofuran was dropwise added, and the mixture was stirred for 2.5 hours. The reaction was stopped with 15 ml of ethyl acetate and an ammonium chloride aqueous solution, the reaction mixture was extracted with ethyl acetate, and the extract was washed with a sodium chloride aqueous solution. The extract was dried over anhydrous magnesium sulfate, the solvent was evaporated off under vacuum, and the residue was purified by silica gel column chromatography (chloroform:methanol (volume ratio)=25:1), to give 3.4 g (yield 27%) of 2,6-dichloro-N-(2,6-dichlorobenzoyl)-N-(5-hydroxymethylpyrid-2-yl)benzamide (e).

In 40 ml of dichloromethane was dissolved 855 mg (1.8 mmol) of 2,6-dichloro-N-(2,6-dichlorobenzoyl)-N-(5-hydroxymethylpyrid-2-yl)benzamide (e), and 905 mg (2.7 mmol) of carbon tetrabromide and 573 mg (2.2 mmol) of triphenylphosphine were added. The mixture was stirred for 2.5 hours, and treated with a saturated sodium hydrogen carbonate aqueous solution. The mixture was subjected to extraction with chloroform, and the extract was washed with a saturated sodium chloride aqueous solution. The solvent was evaporated off under vacuum, and the residue was purified by silica gel column chromatography (hexane:ethyl acetate (volume ratio)=3:1-2:1) to give 631 mg (yield 65%) of 2,6-dichloro-N-(5-bromomethylpyrid-2-yl)-N-(2,6-dichlorobenzoyl)benzamide (f).

In 600 ml of ethanol was dissolved 25.0 g (127 mmol) of 4-hydroxy-3-nitrophenylacetic acid, 3.2 ml of concentrated sulfuric acid was added, and the mixture was refluxed under heat for 6 hours. After the reaction, the solvent was removed under vacuum, and the residue was dissolved in ethyl acetate. The mixture was washed with water, a sodium hydrogen carbonate aqueous solution and a sodium chloride aqueous solution, and then dried over anhydrous sodium sulfate. The solvent was distilled off under reduced pressure, to give 28.3 g (yield 99%) of ethyl 4-hydroxy-3-nitrophenylacetate ester in the form of a yellow solid.

28.2 Grams (125 mmol) of ethyl 4-hydroxy-3-nitrophenylacetate ester was dissolved in 700 ml of acetone, 23.4 ml (376 mmol) of methyl iodide was added in the presence of 86.5 g (626 mmol) of potassium carbonate, and the mixture was refluxed under heat for 3 hours. A solid was filtered off, then the solvent was removed under vacuum, and the residue was dissolved in ethyl acetate. The solution was washed with a sodium chloride aqueous solution and then dried over anhydrous sodium sulfate. The solvent was removed under vacuum, and the residue was purified by silica gel column chromatography (hexane:ethyl acetate (volume ratio)=3:1), to give 29.6 g (yield 99%) of ethyl 4-methoxy-3-nitrophenylacetate ester.

13.5 Grams (56 mmol) of ethyl 4-methoxy-3-nitrophenylacetate ester, 6.1 ml (67 mmol) of isobutyl aldehyde and 1.3 g of 10 wt % palladium carbon were dissolved in 280 ml of methanol, and the mixture was stirred under a hydrogen atmosphere (0.29 MPa) for 14 hours. The palladium carbon was filtered off with cerite, then, the solvent was removed under vacuum, and the residue was purified by silica gel column chromatography (hexane: ethyl acetate (volume ratio)=6:1) to give 14.8 g (yield 100%) of ethyl 3-isobutylamino-4-methoxyphenyl acetate ester in the form of a yellow syrup.

31.2 Grams (117 mmol) of ethyl 3-isobutylamino-4-methoxyphenyl acetate ester was dissolved in 600 ml of dichloromethane, and 15.9 ml (129 mmol) of pivaloyl chloride was added at 0° C. Further, 36.1 ml (259 mmol) of triethylamine was added, and the mixture was stirred at room temperature for 3 hours. The reaction mixture was treated with a sodium hydrogen carbonate aqueous solution and subjected to extraction with chloroform. The extract was washed with a sodium chloride aqueous solution and then dried over anhydrous sodium sulfate. The solvent was removed under vacuum, and the residue was purified by silica gel column chromatography (hexane:ethyl acetate (volume ratio)=3:1) to give 36.2 g (yield 89%) of ethyl 3-[(2,2-dimethylpropionyl)isobutylamino]-4-methoxyphenylacetate ester (g) in the form of a white solid.

Dissolved in 5 ml of tetrahydrofuran was 150 mg (0.43 mmol) of ethyl 3-[(2,2-dimethylpropionyl)-isobutylamino]-4-methoxyphenylacetate ester (g), and 0.26 ml (0.52 mmol) of a solution of 2 mol/l of lithiumdiisopropylamide in heptane, tetrahydrofuran and ethylbenzene was dropwise added at −78° C. The mixture was stirred for 30 minutes, and then a solution of 277 mg (0.52 mmol) of 2,6-dichloro-N-(5-bromomethylpyrid-2-yl)-N-(2, 6-dichlorobenzoyl)benzamide (f) in 5 ml of tetrahydrofuran was dropwise added. The mixture was temperature-increased to room temperature, stirred further for 1 hour, and treated with 1 mol/liter of hydrochloric acid. The reaction mixture was subjected to extraction with ethyl acetate, and the extract was dried over anhydrous magnesium sulfate. The solvent was evaporated off under vacuum, and the residue was purified by silica gel column chromatography (hexane:ethyl acetate (volume ratio)=2:1), to give 245 mg (yield 71%) of ethyl 3-{6-[bis (2,6-dichlorobenzoyl)amino]pyrid-3-yl}-2-{3-[(2,2-dimethylpropionyl)isobutylamino]-4-methoxyphenyl}propionate ester (h)

Dissolved in a solvent mixture of 5 ml of methanol with 5 ml of tetrahydrofuran was 240 mg (0.3 mmol) of ethyl 3-{6-[bis(2,6-dichlorobenzoyl)amino]pyrid-3-yl}-2-{3-[(2, 2-dimethylpropionyl)isobutylamino]-4-methoxyphenyl}propionate ester (h), 49 mg (0.91 mmol) of sodium methoxide was added, and the mixture was refluxed under heat for 17 hours. The solvent was removed under vacuum, and then the reaction mixture was treated with 1 mol/liter of hydrochloric acid. The reaction mixture was subjected to extraction with ethyl acetate and washed with a saturated sodium chloride aqueous solution. The reaction mixture was dried over anhydrous magnesium sulfate, and the solvent was removed under vacuum. The residue was dissolved in a solvent mixture of 5 ml of methanol with 5 ml of tetrahydrofuran, 0.45 ml (0.9 mmol) of a sodium hydroxide (2 mol/liter) aqueous solution was added, and the mixture was stirred for 16 hours. The reaction mixture was treated with 1 mol/liter of hydrochloric acid. The solvent was evaporated off under vacuum, waster was added to the residue, and a precipitate was recovered by filtration. The precipitate was purified by silica gel column chromatography (chloroform:methanol (volume ratio)=20:1-10:1), to give 50 mg (yield 28%) of 3-[6-(2,6-dichlorobenzoylamino) pyrid-3-yl]-2-{3-[(2,2-dimethylpropionyl)isobutylamino]-4-methoxyphenyl}propionic acid (I-a).

The following Table 5 shows physical property values thereof.

Compounds of Examples 2 to 10 shown in the following Tables 5, 6 and 7 were prepared in the same manner as in Example 1. The following Tables 5, 6 and 7 shows physical property values thereof.

TABLE 5

| Example | R² | X² | NMR, MS |
|---|---|---|---|
| 1 | Me  Me Me | —OMe | ¹H-NMR(DMSO-d₆)δ: 0.78-0.95(15H, m), 1.50-1.75(1H, m), 2.57-2.67(1H, m), 3.00-3.20(1H, m), 3.25-3.30(1H, m), 3.84(3H, s), 3.92-4.05(2H, m), 7.00-7.20(2H, m), 7.35-7.48(1H, m), 7.53-7.61(3H, m), 7.70-7.80(1H, m), |

TABLE 5-continued

| Example | R² | X² | NMR, MS |
|---|---|---|---|
| | | | 8.05-8.20(2H, m), 11.23(1H, brs). FABMS: 600(M+H)⁺. |
| 2 | 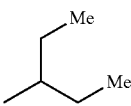 | —OMe | ¹H-NMR(DMSO-d₆)δ: 0.73-0.91(12H, m), 1.44-1.58(1H, m), 1.97-2.22(1H, m), 2.84-3.05(2H, m), 3.21-3.29(1H, m), 3.58-3.69(1H, m), 3.77(3H, s), 3.91(1H, m), 7.03-7.11(2H, m), 7.32(1H, t, J=10.4Hz), 7.42-7.54(3H, m), 7.61(1H, t, J=8.7Hz), 8.01-8.07(2H, m), 11.15&11.16(1H, s), 12.48(1H, brs). FABMS: 586 (M+H)⁺. |
| 3 | 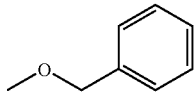 | —OMe | ¹H-NMR(DMSO-d₆)δ: 0.56-0.65(3H, m), 0.72-0.86(9H, m), 1.06-1.56(6H, m), 1.68-1.91(1H, m), 2.81-3.05(2H, m), 3.22(1H, m), 3.75(3H, s), 3.82-3.92(1H, m), 7.00(1H, d, J=18.5Hz), 7.09(1H, d, J=8.9Hz), 7.33(1H, t, J= 6.8Hz), 7.42-7.66(4H, m), 8.00-8.08(2H, m), 11.17&11.18(1H, s), 12.47(1H, brs). FABMS: 614 (M+H)⁺. |
| 4 |  | —OMe | ¹H-NMR(DMSO-d₆)δ: 0.79(3H, d, J=5.3Hz), 0.85(3H, s), 1.47-1.58(1H, m), 2.89-3.05(2H, m), 3.20-3.26(1H, m), 3.42-3.47(1H, m), 3.71(3H, s), 3.81-3.85(1H, ,m), 4.91-5.11(2H, m), 6.99-7.04(2H, m), 7.11-7.30(5H, m), 7.39(1H, m), 7.42-7.56(3H, m), 7.64(1H, d, J=6.9Hz), 8.02-8.13(2H, m), 11.16(1H, s), 12.27-12.58(1H, m). FABMS: 650(M+H)⁺. |

TABLE 6

| Example | R² | X² | NMR, MS |
|---|---|---|---|
| 5 | 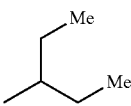 | —OEt | ¹H-NMR(DMSO-d₆)δ: 0.71-0.89(12H, m), 1.26(3H, t, J= 6.8Hz), 1.40-1.65(1H, m), 1.98-2.25(1H, m), 3.02-3.05(2H, m), 3.06-3.32(1H, m), 3.47-3.60(1H, m), 3.92(1H, m), 4.03(2H, q, J=6.9Hz), 7.06(2H, d, J=8.9 Hz), 7.28(1H, brs), 7.46-7.62(4H, m), 8.00-8.05(2H, m), 11.15(1H, s). FABMS: 600(M+H)⁺. |
| 6 | 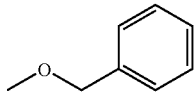 | —OEt | ¹H-NMR(DMSO-d₆)δ: 0.72-0.89(15H, m), 1.27(3H, t, J=6.3 Hz), 1.40-1.70(1H, m), 2.63-2.68(1H, m), 3.00(1H, m), 3.23(1H, m), 3.78-4.06(4H, m), 7.01(2H, d, J=8.3Hz), 7.31(1H, m), 7.42-7.53(3H, m), 7.64(1H, m), 7.99-8.10(2H, m), 11.15(1H, s), 12.46(1H, brs). FABMS: 614(M+H)⁺. |

TABLE 6-continued

[Structure: 2-(3-(N-isobutyl-N-(C(=O)R²))amino-4-X²-phenyl)-2-(pyridyl-NHC(=O)-(2,6-dichlorophenyl))-acetic acid]

| Example | R² | X² | NMR, MS |
|---|---|---|---|
| 7 | isobutyl (CH₂CH(Me)CH₂Me) | —OEt | $^1$H-NMR(DMSO-$d_6$)δ: 0.55-0.67(6H, m), 0.71-0.85(6H, m), 1.17-1.19(2H, m), 1.27(3H, t, J=6.8Hz), 1.35-1.43(2H, m), 1.70-1.91(1H, m), 2.95-3.05(2H, m), 3.21(1H, m), 3.66-3.69(1H, m), 3.88-4.05(4H, m), 7.00(1H, d, J=15.8Hz), 7.06(1H, d, J=8.6Hz), 7.29(1H, m), 7.42-7.65(4H, m), 7.94-8.11(2H, m), 11.16(1H, s), 12.45(1H, brs). FABMS:628 (M+H)⁺. |
| 8 | —CH₂OCH₂Ph (benzyloxymethyl) | —OEt | $^1$H-NMR(DMSO-$d_6$)δ: 0.80(3H, s), 0.84(3H, s), 1.21(3H, s), 1.40-1.65(1H, m), 2.80-3.05(1H, m), 3.06-3.20(2H, m), 3.35-3.50(1H, m), 3.80-4.00(3H, m), 4.90-5.15(2H, m), 6.99-7.05(2H, m), 7.19-7.63(10H, m), 8.02-8.14(2H, m), 11.17(1H, s). FABMS: 664(M+H)⁺. |

TABLE 7

[Structure: 2-(3-(N-isobutyl-N-(C(=O)R²))amino-4-X²-phenyl)-2-(pyridyl-NHC(=O)-(3,5-dichloropyridin-4-yl))-acetic acid]

| Example | R² | X² | NMR, MS |
|---|---|---|---|
| 9 | tert-butyl (C(Me)₃) | —OMe | $^1$H-NMR(DMSO-$d_6$)δ: 0.70-0.88(15H, m), 1.50-1.75(1H, m), 2.48-2.52(1H, m), 2.92-3.07(1H, m), 3.22-3.28(1H, m), 3.77(3H, s), 3.91-3.95(2H, m), 6.98-7.08(2H, m), 7.30-7.38(1H, m), 7.63-7.70(1H, m), 7.95-8.21(2H, m), 8.74(2H, s), 11.35(1H, brs), 12.44(1H, brs). FABMS: 601(M+H)⁺. |
| 10 | tert-butyl (C(Me)₃) | —OEt | $^1$H-NMR(DMSO-$d_6$)δ: 0.71-0.89(15H, m), 1.27(3H, t, J=6.6Hz), 1.35-1.60(1H, m), 2.56-2.76(1H, m), 2.98-3.06(1H, m), 3.21-3.23(1H, m), 3.77-4.06(4H, m), 7.00-7.07(2H, m), 7.27-7.34(1H, m), 7.65-7.68(1H, m), 7.97-8.12(2H, m), 8.74(2H, s), 11.35&11.38(1H, s), 12.47(1H, brs). FABMS: 615(M+H)⁺. |

Test Example 1 VLA-4/VCAM-1 Adhesion Inhibition Test

The compound of the present invention was evaluated for inhibition activity against the adhesion between Chinese hamster ovary cells (CHO cell) transfected with a human VCAM-1 gene and promyelocyte-like cell line HL-60 that exhibiting VLA-4 according to the following method.

The above VCAM-1 expressing CHO cells were placed in a 96-well culture plate in amount of 7×10³ cells per well and cultured in Ham's F-12 medium containing 10 wt % fetal calf serum (FCS) for 3 days until a confluent state was satisfied. The HL-60 cells were re-floated in Hanks' solution containing 0.4 wt % bovine serum albumin (BSA), and 5 μM of 2',7'-bis(carboxyethyl)-5(6)-carboxyfluorescein penta acetoxy methyl ester (BCECF-AM) was added to label the cells. Solutions having various concentrations of each test substance and having an amount of 20 μl each were added to 180 μl each of suspensions of BCECF-labeled HL-60 cells re-floated at a rate of 4×10⁶ cells/ml in the FCS-non-containing RPMI 1640 culture medium, and pre-treated at 37° C. for 15 minutes.

Then, the pre-treated HL-60 cells were stratified in the 96-well plate culturing the VCAM-1 expressing CHO cells at a rate of 2×10⁵ cells per well, and allowed to adhere thereto at 37° C. for 5 minutes. Then, the plate was filled with 0.4 wt % BSA Hanks, covered with a plate sealer and turned upside down. Further, the cells were cultured for 45 minutes. After washing, 1 wt % NP-40-containing PBS was added to destroy the cells, and the thus-obtained supernatants were measured for fluorescence intensity with a cyto Fluor 2300 fluorescence measurement system (supplied by Millipore).

Further, as a blank, 1 wt % NP-40-containing PBS was measured for fluorescence intensity. Further, as standards, a fluorescence-labeled HL-60 floating liquid was added to 1 wt % NP-40-containing PBS at a rate of 2×10⁵, 10⁵, 2×10⁴ and 10⁴ cells/ml, the cells were destroyed, and the thus-obtained supernatants were measured for fluorescence intensity.

Each test substance was measured as described above, and on the basis of the calibration curve prepared from the measurements of the standard, cells in a control and cells adhering to the VCAM-1 expressive CHO cells due to the addition of the test substances were measured for numbers, and cell adhesion inhibition ratios (%) were calculated on the basis of the following equation.

Cell adhesion inhibition ratio (%)=100×[1−(number of adhered cells of groups to which the test substance was added/number of adhered cells of control groups)

The following Table 8 shows 50% inhibition concentrations of the test substances calculated in this Test Example.

TABLE 8

| Example | 50% inhibition concentration (nM) |
|---------|-----------------------------------|
| 1 | 3 |
| 2 | 12 |
| 3 | 33 |
| 5 | 48 |
| 6 | 13 |
| 7 | 7.3 |
| 9 | 2.8 |
| 10 | 1.2 |

When the LPAM-1/VCAM-1 adhesion inhibition test was conducted with regard to Examples 1, 9 and 10, adhesion inhibition activity was found.

INDUSTRIAL UTILITY

According to the present invention, there can be provided a novel 2-phenyl-3-heteroarylpropionic acid derivative or a salt thereof, which is effective for the therapy and prophylactic of diseases caused through VLA-4 and/or LPAM-1, which is excellent in oral absorption and in-vivo moving state and which exhibits VLA-4 and/or LPAM-1 antagonistic activity. According to the present invention, further, there can be provided a VLA-4 and/or LPAM-1 antagonist and pharmaceutical agent, which are useful as a pharmaceutical agent for the therapy or prevention of diseases caused through VLA-4 and/or LPAM-1 such as diseases caused by adhesion and infiltration of leucocyte or diseases in which a VLA-4 and/or LPAM-1 dependent adhesion process plays a certain role.

The invention claimed is:
1. A 2-phenyl-3-heteroarylpropionic acid derivative of the general formula (I),

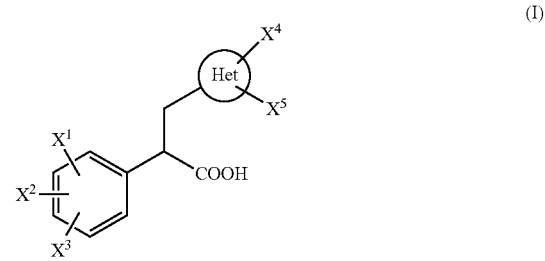

(I)

wherein Het is an aromatic heterocyclic ring selected from the group consisting of pyridinone, indole, pyrrole, thiazole, furan, thiophene, oxazole, pyridine, pyrimidine, pyrazine, quinoline, and phthalimide, and each X1, X2 or X3 is independently a hydrogen atom, a hydrocarbon group that bonds to the benzene ring directly or via oxygen, —N(R¹)COR², in which each of R¹ and R² is independently a hydrogen atom or a hydrocarbon or heteroaryl group which may have an oxygen atom at a terminal bonding site, and R¹ and R² may bond to each other and form a ring that may contain a hetero atom, a double bond or a substituent, provided that when two substituents of X1, X2 and X3 bond to adjacent carbon atoms, the two substituents may bond to each other and form a benzene ring or a methylenedioxy group, and wherein at least one of X4 and X5 in the general formula (I) is a group represented by any one of the general formulae (II) to (V):

(II)

—OCH₂—R¹¹ (III)

—CH═CH—R¹¹ (IV)

—C≡C—R¹¹ (V)

wherein R⁴ is a hydrogen atom or an alkyl group having 1 to 15 carbon atoms and R¹¹ is a group represented by the general formula (VI) or (VII),

(VI)

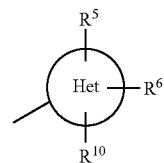

(VII)

wherein each of R⁵ and R⁶ is independently a hydrogen atom, a halogen atom, a nitro group, a cyano group, a hydroxyl group, a carboxyl group or a hydrocarbon or heteroaryl group that bonds to the benzene ring or the aromatic heterocyclic ring directly or through an oxygen atom, a sulfur atom, an oxycarbonyl group, a carbonyl group, a carbonyloxy group, a sulfonyl group or a sulfinyl group, —NR7R8, —N($R^7$)$COR^8$, —N($R^7$)$SO2R^8$, —N($R^7$)$CONR^8R^9$ or —$CONR^7R^8$, in which each of $R^7$, $R^8$ and $R^9$ is independently a hydrogen atom or a hydrocarbon or heteroaryl group which may have an oxygen atom at a terminal bonding site, and $R^7$ and $R^8$ may bond, or $R^8$ and $R^9$ may bond, to each other and form a ring that may contain a hetero atom, a double bond or a substituent, Het is an aromatic heterocyclic ring and $R^{10}$ is a hydrogen atom or an alkyl group having 1 to 15 carbon atoms, or a salt thereof.

2. The 2-phenyl-3-heteroarylpropionic acid derivative or a salt thereof as recited in claim 1, wherein at least one of $X^1$, $X^2$ and $X^3$ in the general formula (I) is —N($R^1$)$COR^2$, an alkyl group, or an alkoxy group.

3. The 2-phenyl-3-heteroarylpropionic acid derivative or salt thereof as recited in claim 2, wherein at least one of $X^1$, $X^2$ and $X^3$ is —N($R^1$)$COR^2$ substituted on the 3-position.

* * * * *